United States Patent [19]

Murtha

[11] 4,123,470

[45] Oct. 31, 1978

[54] BIARYL PRODUCTION

[75] Inventor: Timothy P. Murtha, Bartlesville, Okla.

[73] Assignee: Phillips Petroleum Company, Bartlesville, Okla.

[21] Appl. No.: 804,125

[22] Filed: Jun. 6, 1977

[51] Int. Cl.$^2$ ............................................. C07C 15/14
[52] U.S. Cl. ............... 260/668 D; 260/668 B; 260/668 R
[58] Field of Search ............ 260/668 D, 668 R, 668 B

[56] References Cited

U.S. PATENT DOCUMENTS

| | | | |
|---|---|---|---|
| 3,274,276 | 9/1966 | Lowvar | 260/668 D |
| 3,829,514 | 8/1974 | Zuech | 260/668 R |
| 3,829,515 | 8/1974 | Zuech et al. | 260/668 R |
| 3,829,516 | 8/1974 | Zuech et al. | 260/668 R |
| 3,829,517 | 8/1974 | Zuech | 260/668 R |
| 3,928,481 | 12/1975 | Suggitt | 260/668 D |
| 3,956,183 | 5/1976 | Zuech | 252/441 |
| 3,962,362 | 6/1976 | Suggitt | 260/668 D |

OTHER PUBLICATIONS

R. C. Fuson, Adv. Org. Chem., John Wiley & Sons, N.Y., pp. 252, 264–267, 1950.
Chem. Ab., 43 : 5376e, 1949.
Chem. Ab. 48 : 12017h, 1954.
Rec. Trav. Chim. 70, pp. 403–411, 1951.

*Primary Examiner*—Veronica O'Keefe

[57] ABSTRACT

Aromatic hydrocarbons are converted to biaryl compounds in a two-step process comprising hydroalkylation of the aromatic hydrocarbons to cycloalkyl aromatic hydrocarbons followed by dehydrogenation in the presence of a metal dehydrogenation catalyst and an acidic support to convert the cycloalkyl aromatic hydrocarbons to biaryl compounds. In one embodiment, benzene is hydroalkylated to cyclohexylbenzene, and the cyclohexylbenzene then dehydrogenated to biphenyl.

8 Claims, No Drawings

BIARYL PRODUCTION

This invention relates to a process for the preparation of biaryl compounds. In accordance with another aspect, this invention relates to a process whereby aromatic compounds are subjected to a combination hydroalkylation-dehydrogenation reaction to produce biaryl compounds. In accordance with another aspect, this invention relates to a two-step process for converting monocyclic aromatic hydrocarbons to biaryl compounds by first subjecting the aromatic hydrocarbons to hydroalkylation, followed by dehydrogenation in the presence of a metal dehydrogenation catalyst and an acidic support to produce the corresponding biaryl compounds. In accordance with a specific aspect, this invention relates to a process for converting benzene to biphenyl in a two-step process by hydroalkylating benzene to cyclohexylbenzene and dehydrogenating cyclohexylbenzene to biphenyl.

Biaryl hydrocarbons can be described as compounds having a ring assembly composed of two carbocyclic aromatic hydrocarbon rings joined by one carbon-carbon single bond between carbon atoms of the respective carbocyclic rings. The simplest member of such a series of hydrocarbons is, of course, biphenyl. Biphenyl itself is a compound of well-known utility in the chemical arts. It is used as a chemical intermediate in a variety of syntheses and is also useful as a heat transfer medium component. Heretofore, the production of biaryls such as biphenyl has been plagued by the fact that larger ring assemblies often accompany the desired biaryl. For example, in the production of biphenyl by pyrolyzing benzene, there is often appreciable quantities of terphenyl and higher polyphenyls produced in the process. These by-products often present separation problems in recovering high purity biphenyl and can often be difficult to dispose of even if easily separated from the desired biphenyl. Other known methods of synthesizing biaryls involve the coupling (with dehalogenation) of aromatic halides utilizing metals of various types. These latter methods are restricted almost entirely to laboratory syntheses because of the cost of starting materials involved in such methods of preparation.

Accordingly, an object of this invention is to provide a two-step process for converting aromatic hydrocarbons to biaryl compounds.

Another object of this invention is to provide an improved process for the production of biaryl compounds essentially free of by-product triaryls and higher ring assemblies.

A further object of this invention is to provide a process for producing biaryl compounds in high yield and selectivity.

Another object of this invention is to provide a process for the production of biaryl compounds utilizing inexpensive starting materials and catalysts.

Other objects, aspects, and the several advantages of this invention will become apparent to those skilled in the art upon a study of this disclosure and the appended claims.

In accordance with the invention, a process is provided for converting monocyclic aromatic hydrocarbons to biaryl compounds by hydroalkylation and dehydrogenation in the presence of a metal dehydrogenation catalyst and an acidic support. The instant invention utilizes a two-step process whereby a monocyclic aromatic hydrocarbon is hydroalkylated to produce a cycloalkyl aromatic hydrocarbon in a first step and wherein the cycloalkyl aromatic hydrocarbon product of the first step is treated under dehydrogenation conditions in the presence of a metal dehydrogenation catalyst and an acidic support whereby said cycloalkyl aromatic hydrocarbon is converted to a biaryl compound. The instant invention provides a convenient, selective, and inexpensive method of obtaining biaryl compounds such as biphenyl from aromatic hydrocarbons such as benzene. Both steps of the aforementioned two-step process are carried out in the presence of hydrogen and suitable catalysts to be employed are described more fully below.

As an illustration of the above-described two-step process, benzene is converted to cyclohexylbenzene in a first hydroalkylation step and subsequently the cyclohexylbenzene product of the first step is dehydrogenated in the second step in the presence of a metal dehydrogenation catalyst and an acidic support to produce biphenyl in high yield and selectivity. The biaryl hydrocarbons produced according to the instant invention are essentially free of by-product triaryls and higher ring assemblies. Furthermore, the process of the instant invention utilizes inexpensive monocyclic aromatic hydrocarbons as the starting materials and relatively inexpensive and easily prepared catalysts in both steps of the process.

As indicated above, the first step in the instant process involves the hydroalkylation of monocyclic aromatic hydrocarbons containing from 6 to about 12 carbon atoms per molecule. The desired product from the hydroalkylation reaction is, of course, the cycloalkyl aromatic hydrocarbon, although the product mixture may often contain smaller amounts of monocyclic cycloaliphatic hydrocarbons, as well as isomeric species. Some specific examples of feedstocks suitable for the first step of the instant process are benzene, toluene, the xylenes, and the like, and mixtures thereof. It will, of course, be appreciated that if mixtures of monocyclic aromatic hydrocarbons are utilized as the feed for step 1 that the product from said step 1 and from step 2 will also comprise mixtures of the respective cycloalkyl aromatic hydrocarbons and the biaryl hydrocarbons.

Suitable hydroalkylation catalysts and hydroalkylation reaction conditions are well known in the art, and the instant invention is not dependent upon utilization of a specific hydroalkylation catalyst or specific hydroalkylation reaction conditions. However, it will be generally desirable to utilize hydroalkylation catalysts having high selectivity to the cycloalkyl aromatic product.

Suitable hydroalkylation catalysts and hydroalkylation reaction conditions are disclosed in U.S. Pat. Nos. 3,829,514; 3,829,515; 3,829,516; 3,829,517; and 3,956,183; which patents are hereby incorporated by reference. As set forth in said patents, the hydroalkylation catalyst can comprise a ruthenium halide-active clay catalyst or a rhodium-active clay catalyst. The ruthenium halide-active clay catalyst can be promoted with other metals. Representative reaction conditions disclosed in these patents include a temperature of from about 100° C. to about 250° C., a hydrogen pressure of from about 100 psig to about 2,000 psig (690–13,800 kPa), and space velocities, defined as volume of liquid feed per volume of catalyst per hour (LHSV), of about 0.5 to about 20.

According to one embodiment of the instant invention, the effluent from the hydroalkylation reaction zone of step 1 is contacted, without any separation of the components of said effluent, in the dehydrogenation zone of step 2 to convert the cycloalkyl aromatic hydrocarbon component of said effluent to the biaryl hydrocarbon.

In another embodiment, the effluent from the hydroalkylation reaction of step 1 can be treated by conventional separation procedures to recover the cycloalkyl aromatic hydrocarbon from said effluent in a relatively pure state followed by the treatment of said separated cycloalkyl aromatic hydrocarbon in the dehydrogenation zone of step 2 to obtain the biaryl aromatic hydrocarbon.

Suitable metal catalysts for the dehydrogenation step of the instant invention include those which are known in the art for the conversion of monocyclic cycloaliphatic hydrocarbons to monocyclic aromatic hydrocarbons. Generally, these catalysts are solid materials comprising noble metals such as palladium or platinum or rhodium and the like on acidic support materials such as silica, silica-alumina, alumina, kaolin, and the like. A particularly useful catalyst is platinum on a high purity acidic alumina which has exhibited the desirable combination of high activity and selectivity in the dehydrogenation reaction. The amount of metal in the catalyst composite generally ranges from about 0.05 up to about 5 percent by weight, and preferably from about 0.1 up to about one percent by weight, based on the total catalyst composite.

It is preferred that the dehydrogenation step of the instant invention be carried out in a continuous manner although it is possible to utilize a batch process if desired. In the continuous process, the feedstream entering the dehydrogenation reaction zone is generally fed to the zone at a liquid hourly space velocity (LHSV) of from about 0.5–25, and preferably from about 2–10. The hydrogen flow rate in said continuous process can be expressed in terms of the mole ratio of $H_2$ to cycloalkyl aromatic compound charged to the reaction zone. In general, this ratio will be from about 0.1/1 up to about 20/1, and preferably from about 0.3/1 to about 5/1. Hydrogen pressure will generally range from about 0–2,068 kPa gauge (0–300 psig), and preferably from about 0–1,034 kPa (0–150 psig). The temperature utilized in the dehydrogenation reaction zone is broadly from about 200°–550° C. and preferably from about 350°–450° C.

If desired, inert hydrocarbon diluents such as benzene can be added to the feedstream entering the dehydrogenation reaction zone. Said diluents are often useful to solubilize the biaryl hydrocarbon product in the effluent stream thus preventing deposition of the typically high melting biaryl hydrocarbons on the cooler portion of the process equipment. It will be recognized that when the embodiment is utilized wherein the effluent from the hydroalkylation reaction zone is fed directly to the dehydrogenation step, unreacted starting monocyclic aromatic hydrocarbon can fulfill the function of an inert diluent in the dehydrogenation step.

It is desirable to avoid known poisons for the hydroalkylation catalysts and the dehydrogenation catalysts utilized in steps 1 and 2. Generally speaking, sulfur compounds are recognized as poisons for said catalysts and thus should be avoided in the respective feedstreams to steps 1 and 2.

The effluent from the dehydrogenation reaction zone can be treated by conventional separation procedures such as fractional distillation and recrystallization, as desired, to obtain high purity biaryl hydrocarbon products. It will obviously be possible to recycle unreacted components to either step 1 or step 2 as desired. For example, in the preparation of biphenyl starting with benzene, unreacted benzene in the effluent from the dehydrogenation zone could be recycled to step 1 while unreacted cyclohexylbenzene would be recycled to step 2. Unreacted hydrogen can also be recovered and recycled from the reaction zone effluent to either or both of steps 1 and 2.

EXAMPLE I

In the runs to be described below, the dehydrogenation step is demonstrated. Thus, cyclohexylbenzene which had been previously prepared in hydroalkylation runs and separated in a relatively pure form was admixed with benzene in 50/50 by weight proportions to provide the feed for the dehydrogenation step. In one run, cyclohexylbenzene alone was utilized as the feed to the dehydrogenation step.

The dehydrogenation catalyst utilized in the runs described below was prepared by impregnating 30 grams of a high purity alumina (Catapal alumina from Conoco Oil Company) in the form of 0.16 cm (1/16 inch) diameter extrudate with a solution of 0.3990 grams of chloroplatinic acid ($H_2PtCl_6.6H_2O$) in about 80 ml of absolute ethanol. The ethanol was removed under reduced pressure on a rotary evaporator and the solid material treated with an additional 50 ml of absolute ethanol and the ethanol evaporated again. The impregnated alumina was placed in a muffle furnace and heated from 27° C. to 377° C. under a flow of air overnight. The weight of the catalyst after this heating step was 27.4 grams.

The reactor utilized in the dehydrogenation step was a downflow trickle bed reactor constructed of pipe of about 46 cm (18 inches) in length and 1.43 cm (9/16 inch) in inside diameter. The reactor was equipped for a continuous operation and with heating means for the top, middle, and bottom portion of the reaction zone. Additionally, the system was provided with a preheating means for the feed going to the reaction zone. The reaction system was also equipped with means for adding hydrogen under pressure to the reaction zone. Effluent from the dehydrogenation reaction zone was analyzed from time to time by gas-liquid phase chromatography (GLC). In at least one instance, samples of the dehydrogenation reaction zone were collected and then subjected to a fractional distillation to determine the composition of the effluent from the reaction zone by this method.

The tubular reactor described above was charged with 8.4 grams (15 ml) of the 0.5 weight percent platinum-on-alumina catalyst described above. The dehydrogenation catalyst was reduced at 300° C. under 689 kPa (100 psig) hydrogen at a hydrogen flow rate of 0.32 liters per minute for a period of three hours. The liquid hourly space velocity of the feed to the dehydrogenation reaction zone was in each run 6.7. In Runs 1, 2, and 3, the feed to the dehydrogenation reaction zone was a mixture of benzene and cyclohexylbenzene (50/50 by weight) while in Run 4 the feed to the dehydrogenation reaction zone was cyclohexylbenzene along. The results obtained in the runs mentioned above, as well as other conditions utilized in said runs, are presented below in the table.

TABLE

| Run No. | Temp., °C | H₂Pressure, kPa (gauge) | H₂ Flow Rate, 1/hr. | CHB Conv., Wt. % | Biphenyl Selectivity, Wt. % |
| --- | --- | --- | --- | --- | --- |
| 1 | 223 | 0 | 6.0 | 22.9 | 39.1 |
| 2 | 330 | 0 | 6.6 | 93.5 | 91.6 |
| 3 | 396 | 172 | 6.6 | 98.6 | 95.1 |
| 4 | 402 | 689 | 6.6 | 96.3 | 100 |

The results shown in the above table demonstrate that cyclohexylbenzene alone or in admixture with benzene can be readily converted to biphenyl in high conversion and high selectivity utilizing a platinum-on-alumina dehydrogenation catalyst.

EXAMPLE II

U.S. Pat. No. 3,928,481 discloses the dehydrogenation of cyclohexyl aromatic compounds utilizing a catalyst comprising a Group VIII metal such as platinum on a non-acidic support (columns 4 and 5). Specifically, said patent describes a test in column 5, lines 10–23, for determining whether or not a particular alumina support is acidic or non-acidic. In view of the disclosure of said patent, it was desirable to test the alumina support which was utilized in the invention runs of Example I above. Furthermore, it was also desirable to examine the acidity of the above-mentioned support after it had been treated with potassium hydroxide. Thus, 40 grams of the gamma-alumina support material utilized in the runs of Example I were treated with an aqueous solution of potassium hydroxide (28 grams of 2.9 weight percent KOH). The alumina was allowed to soak in said solution for 4 hours and then dried in 180° C. for 3 hours. This base-treated alumina was then calcined at 1000° F. for 5 hours.

Both the base-treated alumina prepared as described above and the untreated alumina utilized in the runs of the invention were then tested for acidity according to the directions given in column 5 of U.S. Pat. No. 3,928,481. The results obtained in these tests are described below.

| Untreated Alumina | Base-Treated Alumina |
| --- | --- |
| Step 1: | Step 1: |
| Provided 20 ml of dried benzene saturated with phenolphthalein | Provided 20 ml of dried benzene saturated with phenolphthalein. |
| Step 2: | Step 2: |
| Added 2 grams of untreated alumina to above-described benzene. | Added 2 grams of base-treated alumina to above-described benzene. |
| Step 3: | Step 3: |
| Alumina became pinkish-red in color after standing about 5 minutes. | Alumina became very slightly pink in color on standing about 5 minutes. |
| Step 4: | Step 4: |
| Added 5 ml of water to above system. | Added 5 ml of water to above system. |
| Step 5: | Step 5: |
| Mixture became colorless. | Water layer became intensely colored (purple-red). |

The results of the above-described test demonstrate that the alumina utilized as the support material for the invention runs was an acidic alumina whereas the base-treated alumina was non-acidic according to the directions given in said U.S. Pat. No. 3,928,481, column 5.

I claim:

1. A process for the production of biaryl compounds from monocyclic aromatic hydrocarbons which comprises:
   (a) contacting at least one monocyclic aromatic hydrocarbon with hydrogen in the presence of a hydroalkylation catalyst and under hydroalkylation conditions which produce cycloalkyl aromatic hydrocarbons, and
   (b) treating said cycloalkyl aromatic hydrocarbons produced in (a) with hydrogen in the presence of a metal dehydrogenation catalyst on an acidic support and under dehydrogenation conditions which produce biaryl compounds substantially free of by-product triaryls and higher ring assemblies.

2. A process according to claim 1 wherein the effluent from (a) is treated in (b) without any separation of the components of said effluent to convert the cycloalkyl aromatic hydrocarbon components present to the corresponding biaryl hydrocarbon.

3. A process according to claim 1 wherein the effluent from (a) is subjected to separation to separate the cycloalkyl aromatic hydrocarbon from said effluent in a relatively pure state followed by treatment of the separated cycloalkyl aromatic hydrocarbon with hydrogen under dehydrogenation conditions in (b) to obtain the biaryl hydrocarbon.

4. A process according to claim 1 wherein an inert hydrocarbon diluent is present in the feed to (b).

5. A process according to claim 1 wherein (a) said monocyclic aromatic hydrocarbon contains from 6 to about 12 carbon atoms per molecule, said catalyst is a ruthenium halide-active clay or rhodium-active clay catalyst, and said hydroalkylation conditions include a temperature ranging from about 100° C. to about 250° C. and a hydrogen pressure of from about 100 psig to about 2,000 psig (690–13,800 kPa), and (b) said catalyst is a noble metal on an acidic support, and said dehydrogenation conditions include a temperature ranging from about 200° C. to about 550° C. and a mole ratio of hydrogen to cycloalkyl aromatic hydrocarbon of about 0.1 to 1 to about 20 to 1.

6. A process according to claim 1 wherein unreacted aromatic hydrocarbons are recovered from the effluent from (b) and are recycled to (a) and unreacted cycloalkyl aromatic hydrocarbon in the effluent from (b) is recovered and recycled to (b) and unreacted hydrogen is recovered from the effluent of (b) and recycled to (a) and/or (b).

7. A process according to claim 1 for converting benzene to biphenyl which comprises:
   (a) contacting benzene with hydrogen under hydroalkylation conditions which produce cyclohexylbenzene, and
   (b) treating the cyclohexylbenzene produced in (a) with hydrogen in the presence of a catalyst comprising a noble metal on an acidic support under dehydrogenation conditions which produce biphenyl.

8. A process according to claim 7 wherein the catalyst in (b) is platinum-alumina, the temperature in (b) ranges from about 350° C. to about 450° C., and the feed passed to (b) is a mixture of benzene and cyclohexylbenzene.

* * * * *